United States Patent
Marotta et al.

(10) Patent No.: US 6,274,159 B1
(45) Date of Patent: Aug. 14, 2001

(54) SURFACE MODIFIED SILICONE DRUG DEPOT

(75) Inventors: James S. Marotta, Almond, NY (US); Christopher D. Batich, Gainesville; Nancy S. Hardt, Micanopy, both of FL (US)

(73) Assignee: University of Florida, Gainesville, FL (US)

( * ) Notice: Subject to any disclaimer, the term of this patent is extended or adjusted under 35 U.S.C. 154(b) by 0 days.

(21) Appl. No.: 09/429,396

(22) Filed: Oct. 28, 1999

Related U.S. Application Data

(60) Provisional application No. 60/105,982, filed on Oct. 28, 1998.

(51) Int. Cl.[7] ................................. A61F 2/02; A61F 2/28
(52) U.S. Cl. ........................ 424/426; 523/114; 523/115; 624/16
(58) Field of Search ..................... 424/426; 523/114, 523/115; 604/16

(56) References Cited

U.S. PATENT DOCUMENTS

| | | |
|---|---|---|
| 4,171,544 | 10/1979 | Hench et al. . |
| 4,234,972 | 11/1980 | Hench et al. . |
| 4,322,398 | 3/1982 | Reiner et al. . |
| 4,331,651 | 5/1982 | Reul et al. . |
| 4,652,459 | 3/1987 | Engelhardt . |
| 4,775,646 | 10/1988 | Hench et al. . |
| 4,851,046 | 7/1989 | Low et al. . |
| 4,882,149 | 11/1989 | Spector . |
| 4,883,484 | 11/1989 | Shepherd et al. . |
| 5,074,916 | 12/1991 | Hench et al. . |
| 5,374,427 | 12/1994 | Stille et al. . |
| 5,728,753 | 3/1998 | Bonfield et al. . |
| 5,972,384 | * 10/1999 | Thut et al. ........................ 424/426 |

* cited by examiner

Primary Examiner—Carlos A. Azpuru
(74) Attorney, Agent, or Firm—Miles & Stockbridge; Dennis P. Clarks

(57) ABSTRACT

An improved implantable pharmaceutical depot for the prolonged release of at least one biologically active substance, the depot comprising a polymeric carrier and the biologically active substance, the improvement wherein the depot is coated or surface modified with a biologically active and biocompatible glass, glass-ceramic or ceramic material, the coating or modified surface being capable of forming a bond to soft tissue upon implantation. Methods for forming the biologically active and biocompatible glass, glass-ceramic or ceramic coating or modified surface on the silicone based depot are also disclosed.

4 Claims, 3 Drawing Sheets

SURFACE MODIFIED SILICONE DRUG DEPOT

BACKGROUND OF THE INVENTION

1. Related Application

Reference is hereby made to provisional patent application Ser. No. 60/105,982 filed Oct. 28, 1998, upon which the claim of domestic priority is based herein.

2. Field of the Invention

The present invention relates to drug depot or delivery systems.

3. Description of the Prior Art

The introduction of pharmaceutical agents and the like into a specific site within the body of a patient over a requisite time period by injection or infusion has been proven to be impractical. The predictable, controlled delivery of selected molecules into specific sites in the body is, therefore, preferably accomplished by injection or incorporation of the molecules into a "drug delivery system" or "drug depot" which is implanted into that site. Materials previously proposed to release therapeutic agents into bone tissue, for example, include a variety of resorbable and non-resorbable polymers including polylactic acid and polymethylmethacrylate, and synthetic calcium phosphates including the mineral hydroxyapatite and the compound tricalcium phosphate.

One of the more widely used materials for the construction of such depots are the silicone rubbers, e.g., Norplant® marketed by Wyeth-Ayerst. Drug depots constructed of silicone rubbers suffer, however, from the disadvantage that fibrous scar tissue capsules tend to form around the devices following implantation. This scar capsule is not well vascularized and hinders both the release and availability of the drug from the system. Drug levels have been shown to be reduced by as much as 75% after 21 days implantation [Munro et al, *Contraception*, Vol. 54, pages 43–53 (1996)].

The lack of biocompatibility of implantable materials has been described as being the main problem in the development of long-term drug delivery systems [Park et al, *Pharmaceutical Res.*, Vol. 13, pages 1 770–1776 (1996)]. Current devices consist of silicone tubes filled with the desired drug or agent. When these are implanted, the drug slowly diffuses through the silicone and into the surrounding tissue. The above-noted decreased availability of drug due to incompatibility of the carrier system has a high degree of variation among individuals, thus requiring a large initial drug loading and making the calculation of required drug loading a difficult problem to overcome. Improved availability of the drug to the surrounding tissue would improve the reliability of these devices and could reduce the amount of the drug needed for sustained therapeutic delivery, thereby increasing the performance of the device, reducing the possible side effects of variable drug levels released from the implant, and reducing the cost and size associated with the device.

Despite these complications, many types of drugs have been delivered using silicone depots. The following table sets forth a representative number of examples of drugs having a variety of therapeutic effects that have been incorporated heretofore in silicone depots.

| Name | Category | Drug | Duration |
|---|---|---|---|
| Norplant ® (Wyeth-Ayerst) | contraception | lovonorgestrel | 5 years |
| Uniplant ® (South to South Corp.) | contraception | nomegstrol acetate | 2 years |
| Experimental device [Vanin et al, Am. J. Obstet. Gynecol., Vol. 173, pages 1491–1498 (1995)] | hormone therapy | estradiol, norethindrone or norgestimate | 11 months |
| Experimental device [Milligan et al, Reprod. Fertil. Dev., Vol. 6, pages 235–239 (1994)] | hormone therapy | progesterone | |
| Experimental device [Cohen et al, J. Reprod. Fertil., Vol. 99, pages 219–223 (1993)] | contraception | oestradiol | |
| Experimental device [Becker, Brain Res., Vol. 508, pages 60–64 (1990)] | behavior asymmetry | dopamine | 2 months |
| Experimental device [Wang, J. Biomed. Eng., Vol. 15, pages 106–112 (1993)] | hyperglycemia | insulin | |
| Experimental device [Claus et al, Prostate, Vol. 22, pages 199–215 (1993)] | human benign prostatic hyperplasia | testosterone and beta-estradiol | 4 weeks |

It is an object of the present invention to provide improved silicone rubber drug depot systems which are not subject to the above-noted disadvantages.

SUMMARY OF THE INVENTION

The above and other objects are realized by the present invention, one embodiment of which relates to an improved implantable pharmaceutical depot for the prolonged release of at least one biologically active substance, the depot comprising a carrier constructed of materials such as silicone and the biologically active substance, the improvement wherein the depot is coated with or surface modified by a biologically active material such as a biocompatible glass, glass-ceramic or ceramic material, the coating or modified surface being capable of forming a bond to soft tissue upon implantation.

Another embodiment of the invention relates to methods for forming the coating or surface modification comprising the biologically active and biocompatible glass, glass-ceramic or ceramic on the silicone based depot.

One method of forming the improved depot is to form a coating of the silicone or other suitable polymer and bioactive glass, glass-ceramic or ceramic on the biologically active substance containing depot. Another suitable method comprises incorporating the bioactive glass, glass-ceramic or ceramic in the silicone or other suitable polymer of construction during formation of the depot itself and then removing sufficient silicone (or other polymer) from the surface of the depot system to expose particles of the bioactive glass, glass-ceramic or ceramic thereon.

DETAILED DESCRIPTION OF THE INVENTION

Figure 1:
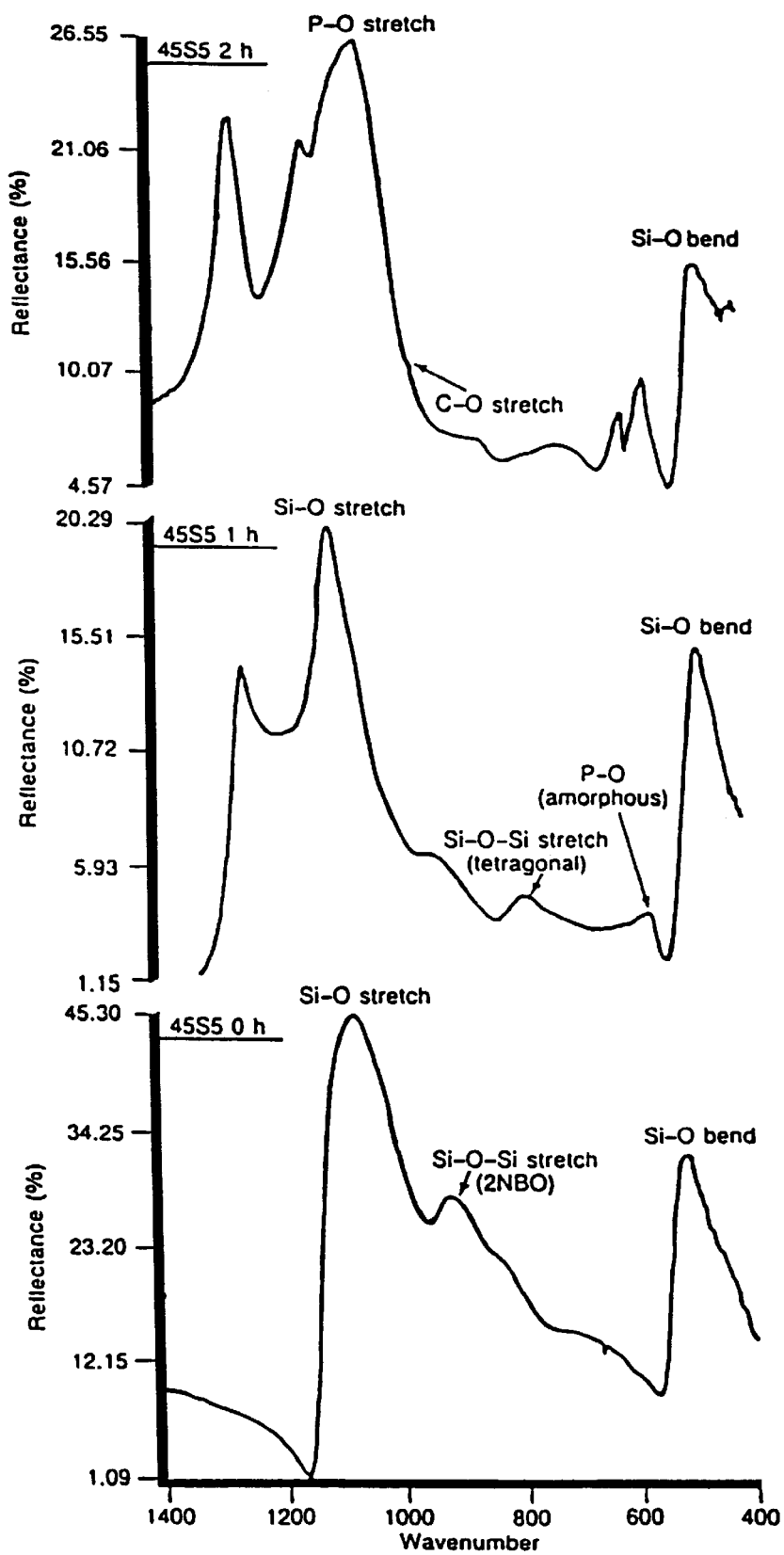
FIG. 1 is an FTIR spectra of a 45s5 Bioglass® implant after 0, 1 and 2 hours in TBS at 37° C. [Hench, *J. Am. Ceram. Soc.*, Vol. 74, pages 1487–1510 (1991)].

It has unexpectedly been found that the biologically active and biocompatible glass, glass-ceramic and ceramic (hereinafter referred to as "bioactive glass") bonds directly to surrounding soft tissue following implantation, thereby inhibiting or preventing the formation of the fibrous scar tissue capsule normally associated with the implantation of silicone materials. The presence of healthy tissue surrounding the depot improves the bioavailability of the contained biologically active substance to the vascular system. Most unexpectedly, it has been found that the bioactive glass coating does not impede diffusion of biologically active substance molecules out of the silicone system and into the subject patient's system.

Any of the polymeric materials utilized for the construction of implantable devices may be used in the practice of the invention. Exemplary of silicone materials are those used in Norplant® (Wyeth-Ayerst), Uniplant® (South to South Corp.), Silgel® (Wacker Chemie GmbH), and the like. Generally, the silicone implantable depots are constructed of polydimethylsilicone (PDMS). A typical such material is dimethylpolysiloxane (Silgel® 601, Wacker Chemie GmbH), an addition cross-linking two-component composition of nine pats of component A and one part of component B. Dimethyldiphenylpolysiloxane, dimethylpolysiloxanol or silicone copolymers may also be employed.

It will be understood, however, by those skilled in the art that the device may also be constructed of any other suitable polymeric material therefor which is compatible with bioactive glasses, glass-ceramics or ceramics. Exemplary of such other polymeric materials are the porous, ethylene/vinyl acetate copolymers which have been utilized to construct depots for the implantable release of hydrophilic biologically active substances such as proteins through the pores thereof.

It will also be understood that any biologically active substance compatible with the silicone carrier may be utilized in the practice of the invention. Exemplary of suitable substances are steroids, hormones, antibiotics, chemotherapeutical agents, prostaglandins, vitamins, contraceptives, behavior modification agents, and the like.

Those skilled in the art are aware of conventional methods for the formation of silicone/active substance depot systems and any such methods may be used to prepare the devices suitable for coating or modification with bioactive material according to the invention. The artisan is also aware of the amounts of active substances to be included in the depot devices, as well as the parameters of construction and methods for their implantation in suitable hosts.

The bioactive material used to coat the silicone depot devices of the invention may comprise any of the known materials, as well as those yet to be discovered which form a bond to soft tissue upon implantation. Exemplary of such bioactive materials are those described in U.S. Pat. Nos. 4,171,544; 4,234,972; 4,775,646; 4,851,046; 5,074,916 and 5,728,753, the entire contents and disclosures of which are incorporated herein in their entirety by reference thereto. Typical of suitable bioactive glasses are those having the following weight percentage composition:

| Composition | Weight Percentage |
| --- | --- |
| $SiO_2$ | 40–52 |
| CaO | 10–50 |
| $Na_2O$ | 10–35 |
| $P_2O_5$ | 2–8 |
| $CaF_2$ | 0–25 |
| $B_2O_3$ | 0–10 |

The coating or layer of bioactive material on the depot device may be any desired thickness, generally in the range of from about 20 microns to several millimeters and, preferably, from about 0.02 mm to about 1.0 mm.

In the following non-limiting examples, the invention is illustrated employing silicone as the polymeric material. Generally, silicone medical devices are constructed employing two-component liquid silicone precursor systems which are commercially available. Upon mixing and subsequent sequent thermal treatment, the two-component system cures into the solid silicone material having any desired shape or configuration.

The bioactive glass, glass-ceramic or ceramic, in particulate or fiber form, is preferably admixed with the two-component liquid silicone precursor system and applied as a coating on the depot device (which, in this case, is also preferably constructed of silicone; preferably, the same silicone). Upon curing, a hardened, solid surface coating of the bioactive material/silicone is formed on the depot device.

Alternatively, the depot device may be coated with the liquid two-component silicone precursor system and then the particles or fibers of bioactive glass, glass-ceramic or ceramic applied thereover. Upon thermal curing, the bioactive fibers or particles are embedded on the surface of the cured silicone coating.

Another method involves incorporating the bioactive material in the silicone system utilized to mold the depot device. Upon curing, sufficient silicone is abraded or dissolved away from the surface of the depot to expose the particles or fibers of bioactive material on the surface thereof.

EXAMPLE 1

A fully cured sheet of silicone (1–2 mm thick) is first made using a two-part silicone mix (dimethylpolysiloxane) and the recommended curing procedure (150° C. for 24 hours under vacuum). A solution of uncured silicone in a compatible solvent is made (5–20%) by mixing the two silicone parts with hexane solvent (suitable solvents include short chain alkanes, cyclic alkanes and chlorinated solvents, e.g., hexane, pentane, octane, chloroform, methylene chloride, trichloromethane). This solution is then either sprayed or poured onto the surface of the cured silicone sheet. The solvent is allowed to evaporate, leaving an uncured silicone layer that is 20 to 40 μm (0.02 to 0.04 mm) thick. Bioglass® 45s5 powder is then applied to the uncured surface. This coated silicone sheet is then placed in an oven at 150° C. for 24 hours to cure the silicone on the surface. The resulting material has the bulk properties of a silicone elastomer. Bioglass® particles are attached to and protruding from the surface. This surface has been shown to produce a hydroxyapatite crystalline layer on both the Bioglass® particle and the silicone surface between particles, when placed in simulated body fluid (SBF) at 37° C. for a period of 10 days.

The formation of a hydroxy carbonate apatite (HCA) layer at the surface of a bioactive glass is essential for bonding to bone or soft tissue. It is assumed that this HCA layer would prevent the formation of a fibrous capsule around the implant. Fourier Transform Infrared (FTIR) spectroscopy can be used to monitor the formation of HCA on the surface of the bioactive glass. Characteristic FTIR spectra of 45s5 Bioglass® reacted in SBF at 37° C. are shown in FIG. 1.

EXAMPLE 2

To evaluate the bioactivity of coated samples produced using this technique, in vitro testing of each sample was conducted in a solution of SBF at 37° C. for 20 hours and 10 minutes.

Figure 2:
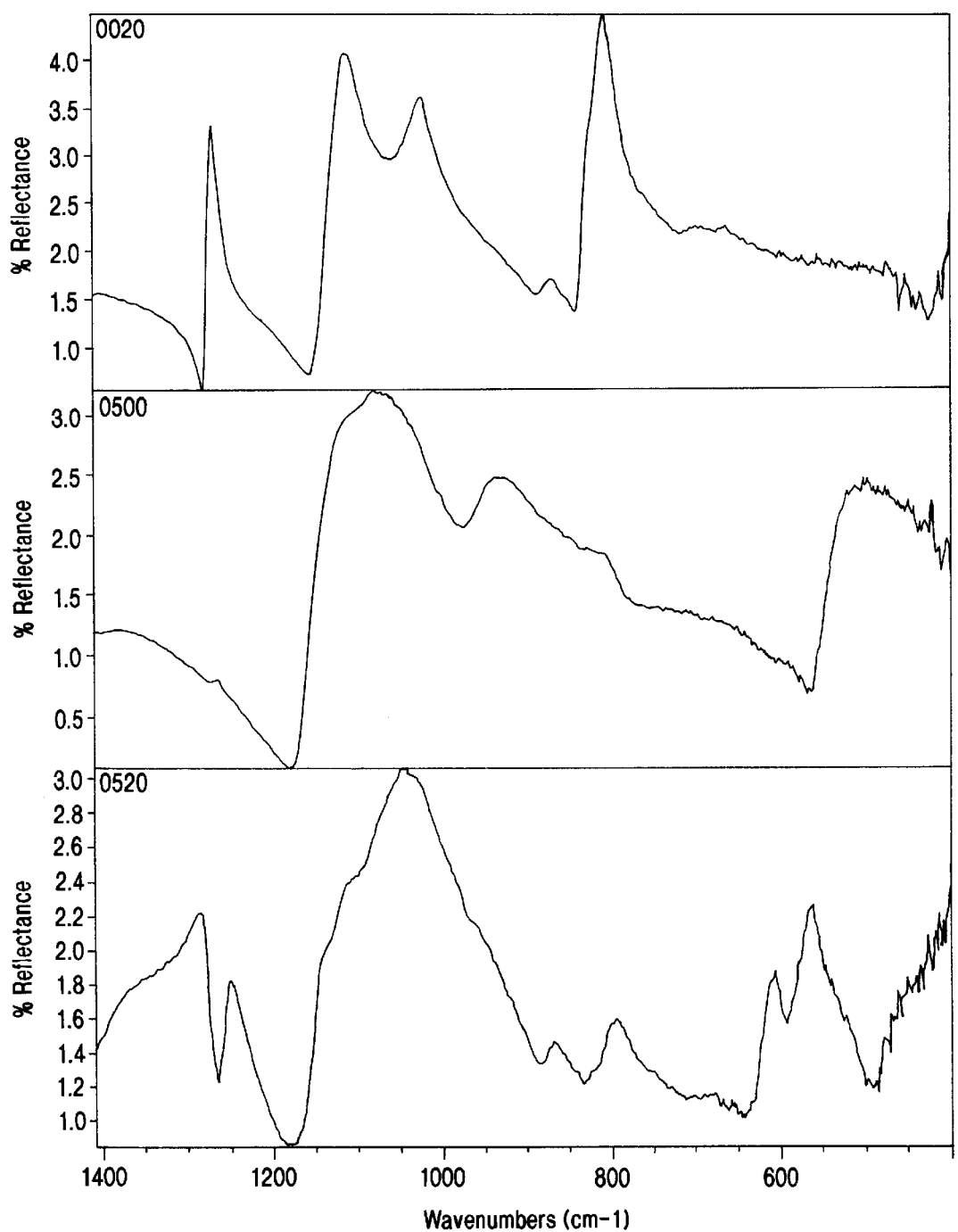
FIG. 2 is an FTIR spectra of Bioglass®-coated silicone samples. From the top, the samples are uncoated silicone reacted for 20 hours in SBF at 37° C., silicone coated with 0.5 g Bioglass® per 25 cm² of silicone unreacted, and silicone coated with 0.5 g Bioglass® per 25 cm² of silicone reacted for 20 hours in SBF at 37° C. The formation of an hydroxyapatite layer can be seen in the bottom spectrum (see double peak at 600 cm$^{-1}$).
Figure 3:
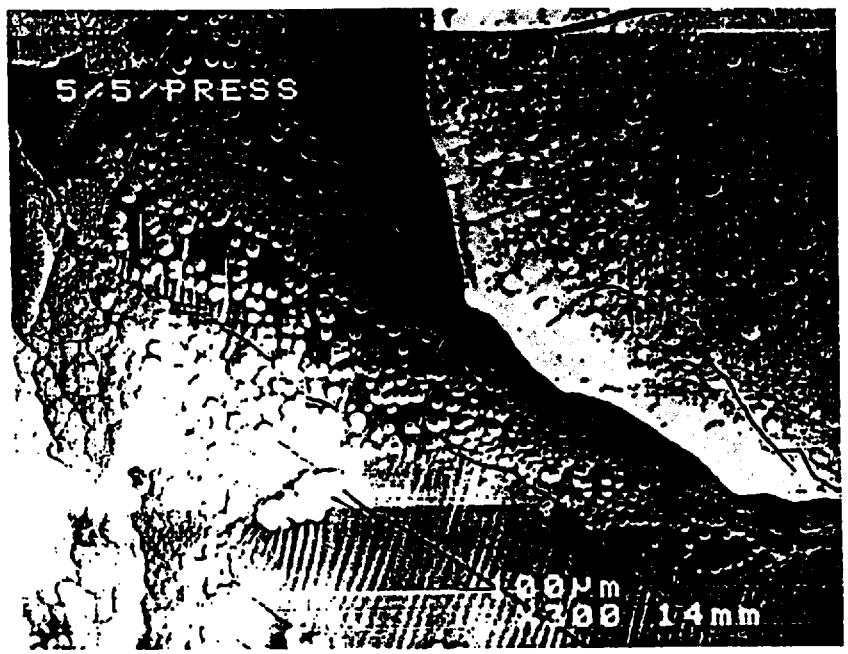
FIG. 3 depicts a surface analysis using low voltage SEM and shows hydroxyapatite crystals on both Bioglass® particles (top right) and on silicone between particles (middle) when reacted for 10 days in SBF at 37° C. Bioglass® powder used was 45s5 in the 710–900 micron size range.
Figure 4:
FIG. 4 depicts a surface analysis using low voltage SEM and shows hydroxyapatite (HA) crystals on silicone coated with Bioglass®. Concentration of HA crystals is greatest next to Bioglass® particles (top left). Samples reacted for 10 days in SBF at 37° C.

The FTIR spectra of Bioglass® coated silicone samples at each time period was measured using a diffuse reflectance stage. Comparison of the Si-O stretch, P-O stretch and P-O bend peaks confirmed the formation of a crystalline HCA layer on the surface of the coated silicone samples (FIG. 2). Surface analysis using low voltage SEM (2 kV) showed HCA particles on both the Bioglass® particles and on the silicone between the particles (FIGS. 3 and 4). This indicates the bioactivity of both the particle and the silicone surface.

We claim:

1. An improved pharmaceutical depot adapted for implantation in a human or non-human animal for the prolonged release therewithin of at least one biologically active substance, said depot comprising a silicone carrier and incorporated therein said biologically active substance, the improvement wherein said depot is coated with a biologically active and biocompatible glass, glass-ceramic or ceramic material comprising at least about 40 weight percent silicon dioxide, said glass coating being capable of forming a bond to soft tissue upon implantation.

2. The depot of claim 1 wherein said biologically active and biocompatible glass, glass-ceramic or ceramic has the following weight percentage composition:

| Composition | Weight Percentage |
| --- | --- |
| $SiO_2$ | 40–52 |
| CaO | 10–50 |
| $NaO_2$ | 10–35 |
| $P_2O_5$ | 2–8 |
| $CaF_2$ | 0–25 |
| $B_2O_3$ | 0–10. |

3. The depot of claim 1 wherein said coating of said biologically active and biocompatible glass, glass-ceramic or ceramic has a thickness of from about 0.02 mm to about 1.0 mm.

4. The depot of claim 1 wherein said biologically active substance is a steroid, hormone, antibiotic, chemotherapeutical agent, prostaglandin, vitamin, contraceptive or behavior modification agent.

* * * * *

UNITED STATES PATENT AND TRADEMARK OFFICE
CERTIFICATE OF CORRECTION

PATENT NO. : 6,274,159 B1
DATED : August 14, 2001
INVENTOR(S) : James S. Marotta et al.

It is certified that error appears in the above-identified patent and that said Letters Patent is hereby corrected as shown below:

Column 6,
Line 24, column entitled "Composition", delete "$NaO_2$" and replace with -- $Na_2O$ --.

Signed and Sealed this

Eighth Day of October, 2002

Attest:

Attesting Officer

JAMES E. ROGAN
Director of the United States Patent and Trademark Office